US006273867B1

(12) United States Patent
Glazer

(10) Patent No.: US 6,273,867 B1
(45) Date of Patent: Aug. 14, 2001

(54) WATER THERAPY BACK TRACTION APPARATUS

(76) Inventor: Henry R. Glazer, 860 Lower Ferry Rd., Trenton, NJ (US) 08628

(*) Notice: Subject to any disclaimer, the term of this patent is extended or adjusted under 35 U.S.C. 154(b) by 0 days.

(21) Appl. No.: 09/425,400

(22) Filed: Oct. 22, 1999

(51) Int. Cl.$^7$ .......... A61F 5/00

(52) U.S. Cl. .......... 602/32; 482/111

(58) Field of Search .......... 602/32–36; 601/158; 482/55, 39, 41, 111; 441/116, 136

(56) References Cited

U.S. PATENT DOCUMENTS

D. 251,202 2/1979 Charewicz .
1,915,371 * 6/1933 Lowman .
3,850,165 11/1974 Throner .
3,889,304 6/1975 Loren .
3,981,484 9/1976 James .
4,001,899 1/1977 Mathis .
4,102,336 7/1978 Wiener et al. .
4,149,712 4/1979 Murphy .
4,183,106 1/1980 Grimes et al. .
4,283,803 8/1981 Krumbeck .
4,365,623 12/1982 Wilhelm et al. .
4,551,108 * 11/1985 Bass .......... 441/116
4,588,155 5/1986 James .
4,665,572 5/1987 Davidson et al. .
4,700,696 10/1987 Schoffstall .
4,712,788 12/1987 Gaudreau, Jr. .
4,722,329 2/1988 Kalvag .
4,875,673 10/1989 Erickson .
4,903,926 2/1990 McNarry et al. .
4,930,169 6/1990 Davison .
4,941,216 7/1990 Boublil .
5,050,863 9/1991 Yacoboski .
5,078,126 1/1992 Perry .
5,218,727 6/1993 Krumbeck .
5,244,393 9/1993 Perry .
5,329,651 7/1994 Mardero et al. .
5,333,322 8/1994 Weir .
5,367,721 11/1994 Boyles .
5,406,653 4/1995 Todor .
5,432,961 7/1995 Horton .
5,465,433 11/1995 Nolan .
5,647,826 7/1997 Butler .
5,715,545 2/1998 Forwick .
5,752,899 5/1998 Ballard .
5,885,194 3/1999 Wasserman et al. .
5,991,651 * 11/1999 LaBarbera .......... 600/415
6,033,351 * 3/2000 Sizemore .......... 482/111

FOREIGN PATENT DOCUMENTS 105-229-A * 11/1983 (SU) .

* cited by examiner

*Primary Examiner*—Justine R. Yu
(74) *Attorney, Agent, or Firm*—Sperry, Zoda & Kane

(57) ABSTRACT

An apparatus for providing back traction in a water therapy environment is disclosed which includes a back support member extending vertically within a body of water such as a swimming pool including two arms extending outwardly therefrom to be placed under the arms of a user while the user's back is in contact with the back support member. A suspension apparatus lifts the back support member and both arms to a limited extent while a user is positioned within the user receiver zone defined between the arms at a slightly elevated position to provide a controllable amount of downwardly directed traction force upon the back of the user. Most of the user's weight is supported by the water and very active control of the amount of traction force can be achieved. The present apparatus is disclosed in a permanent embodiment as well as an embodiment detachably securable with respect to a swimming pool ladder.

10 Claims, 4 Drawing Sheets

WATER THERAPY BACK TRACTION APPARATUS

BACKGROUND OF THE INVENTION

1. Field of the Invention

The present invention deals with the field of traction devices for use in treatment of back pain. Such back pain is a very widely experienced malady throughout the human race and many therapy devices or medical procedures have been devised to attempt to deal with such associated back pain.

Many of these back pain treatment devices include some type of a therapy and some also include therapy in a water environment such as a swimming pool where a portion of the user's weight is eliminated by buoyancy.

2. Description of the Prior Art

Numerous patents have been devised for the purposes of back traction treatment some of which includes water therapy such as shown in U.S. Pat. No. 3,850,165 patented Nov. 26, 1974 to G. Throner on a "Portable Traction System"; and U.S. Pat. No. 3,889,304 patented Jun. 17, 1975 to Jan Loren and assigned to Soderberg Tollam AB on a "Bathing Device For Invalided Persons"; and U.S. Pat. No. 3,981,484 patented Sep. 21, 1976 to D. R. James on a "Lifting Apparatus"; and U.S. Pat. No. 4,001,899 patented Jan. 11, 1977 to C. D. Mathis on a "Combined Swimming And Therapy Pool"; and U.S. Pat. No. 4,102,336 patented to I. Wiener et al on Jul. 25, 1978 on an "Apparatus For Traction Therapy"; and U.S. Design Pat. No. 251,202 patented Feb. 27, 1979 to B. Charewicz on an "Invalid's Treatment Basin"; and U.S. Pat. No. 4,149,712 patented Apr. 17, 1979 to R. J. Murphy on a "Physical Exercise Apparatus"; and U.S. Pat. No. 4,183,106 patented Jan. 15, 1980 to G. Grimes et al and assigned to Gary E. Grimes on a "Swimming Pool Lift For The Handicapped"; and U.S. Pat. No. 4,283,803 patented Aug. 18, 1981 to K. Krumbeck and assigned to The Cheney Company, Inc. on a "Process For Immersing In A Swimming Pool Disabled Persons Using A Wheelchair"; and U.S. Pat. No. 4,365,623 patented Dec. 28, 1982 to T. G. Wilhelm et al and assigned to Tru-Exe Manufacturing Co. on an "Apparatus To Exert Traction In Traction Therapy"; and U.S. Pat. No. 4,588,155 patented May 13, 1986 to D. R. James and assigned to James Industries Limited on "Supports For Hoists"; and U.S. Pat. No. 4,665,572 patented May 19, 1987 to P. Davidson et al on a "Swimming Pool Therapy Apparatus"; and U.S. Pat. No. 4,700,696 patented Oct. 20, 1987 to C. D. Schoffstall on a "Method And Apparatus For Applying Traction"; and U.S. Pat. No. 4,712,788 patented Dec. 15, 1987 to C. Gaudreau, Jr. on an "Aquatic Exercise Apparatus"; and U.S. Pat. No. 4,722,329 patented Feb. 2, 1988 to J. B. Kalvag on an "Apparatus For The Treatment Of Patients With Lumbar Back Ailments Or The Like In A Water Environment"; and U.S. Pat. No. 4,875,673 patented Oct. 24, 1989 to C. Erickson and assigned to 501 Hydrosplash Enterprises, Inc. on an "Aquatic Exercise Device"; and U.S. Pat. No. 4,903,926 patented Feb. 27, 1990 to D. G. McNarry et al and assigned to Poolside Peripherals Ltd. on a "Detachable Immersible Support For Supporting Articles In A Swimming Pool"; and U.S. Pat. No. 4,930,169 patented Jun. 5, 1990 to K. Davison on an "Apparatus For Patient Hydrotherapy And Manipulative Treatment By A Therapist"; and U.S. Pat. No. 4,941,216 patented Jul. 17, 1990 to D. Boublil on a "Lift For Giving Access To The Water In A Swimming Bath Or A Re-Education Pool"; and U.S. Pat. No. 5,050,863 patented Sep. 24, 1991 to A. Yacoboski on an "Exercise Chair For Use In Swimming Pool"; and U.S. Pat. No. 5,078,126 patented Jan. 7, 1992 to L. Perry on a "Flotation Controlled Spinal Decompression"; and U.S. Pat. No. 5,218,727 patented Jun. 15, 1993 to K. Krumbeck and assigned to Industrial Design & Mfg. Inc. on an "Above Ground Spa Lift For The Handicapped"; and U.S. Pat. No. 5,244,393 patented Sep. 14, 1993 to L. R. Perry on a "Flotation Controlled Spinal Decompression"; and U.S. Pat. No. 5,329,651 patented Jul. 19, 1994 to S. G. Mardero et al and assigned to Fiat Products Ltd. on a "Bathing Apparatus For The Infirm"; and U.S. Pat. No. 5,333,322 patented Aug. 2, 1994 to D. H. Weir and assigned to Fox Pool Corporation on an "Add-On Seat Module For Swimming Pool"; and U.S. Pat. No. 5,367,721 patented Nov. 29, 1994 to M. J. Boyles and assigned to BioCare Laboratories, Inc. on a "Lift Apparatus And Method For Transporting A Passenger Into And Out Of A Swimming Pool"; and U.S. Pat. No. 5,406,653 patented Apr. 18, 1995 to F. A. Todor on an "Adjustable Inflatable Body Cradle For Use In Water"; and U.S. Pat. No. 5,432,961 patented Jul. 18, 1995 to L. C. Horton and assigned to Clint Horton, II on a "Lifting Apparatus To Provide Unassisted Pool Access For Disabled Persons"; and U.S. Pat. No. 5,465,433 patented Nov. 14, 1995 to J. D. Nolan on a "Seat Lift"; and U.S. Pat. No. 5,647,826 patented Jul. 15, 1997 to B. FR. Butler on an "Aquatic Exercise And Rehabilitation Device"; and U.S. Pat. No. 5,715,545 patented Feb. 10, 1998 to R. Forwick on a "Bathing Aid"; and U.S. Pat. No. 5,752,899 patented May 19, 1998 to T. Ballard on an "Aquatic Exercise And Therapeutic System"; U.S. Pat. No. 5,885,194 patented Mar. 23, 1999 to J. F. Wasserman et al and assigned to Hydroforce, Inc. on an "Attachment System For Suspending An Exercise And/Or Therapy Apparatus In A Pool Of Liquid".

SUMMARY OF THE INVENTION

The present invention provides a water therapy back traction apparatus usable with swimming pool water which includes a surrounding decking and a conventional ladder with hand rails and steps. It preferably includes a back support member extending generally vertically for receiving the back of a user in contact therewith for supporting thereof. In this permanent embodiment the back member includes an open frame member to facilitate water flow therethrough and comfort of the user. It also includes a first arm detachably secured to the back support member and extending outwardly therefrom approximately horizontal to a position beneath the arm of a user. A first arm adjustment apparatus is also included for providing adjustability and positioning of the first arm with respect to the back support member. A second arm is also detachably secured to the back support member extending outwardly therefrom in an approximately horizontally extending direction and is positionable beneath the arm of a user to facilitate supporting of the user. This second arm is preferably located at a position spatially disposed from the first arm in order to define a user receiving zone therebetween and along with back support member.

A second arm adjustment apparatus is included which provides adjustability and positioning of the second arm with respect to the back support member in order to accommodate different sizes of users by varying the lateral size of the user receiving zone.

A suspension apparatus is also preferably included which is secured to the swimming pool and is attached to the back support member for suspending both this member and the user at least partially within the swimming pool at a slightly elevated position in order to impart traction therapy forces upon the back of a user.

The suspension apparatus in particular includes multiple mounting legs attached to and supported by the decking adjacent the swimming pool. A boom is secured to the mounting leg members and extends outwardly over the water of the swimming pool. This boom preferably includes a mounting aperture extending generally vertically therethrough and a set screw. A mounting shaft is movably mounted extending through the vertically extending aperture and is detachably securable in position by tightening of the set screw. This mounting shaft is secured to the back support member for varying the vertical position thereof and, in particular, the relative vertical position thereof with respect to the water level.

In another embodiment of the present invention the water therapy back traction apparatus is detachably securable with respect to a conventional ladder of a swimming pool. This apparatus includes a back support member which extends generally vertically for receiving the back of a user in abutment therewith and for facilitating support. It also includes a first arm slot and a second arm slot extending horizontally and defined within the back support member. A ladder attachment device is attached to the back support member in order to selectively affix it securely with respect to a ladder extending into the swimming pool water. This ladder attachment means preferably includes a main support bar detachably securable to the back support member such that it extends outwardly therefrom. The support bar is detachably secured thereto to facilitate adjustment in the vertical direction in order to control the relative position of the back support member with respect to the water level of the swimming pool and thereby provide control of the downwardly directed traction therapy forces. The main support bar is adapted to be positioned in abutment with a ladder step for supporting the back support member with respect thereto. A rail securement device is also included attached to the back support member and extending outwardly therefrom adjacent the main support bar in such a manner as to engage each of the vertical ladder hand rails and further affix the back support member detachably with respect to the ladder. These rail securement devices preferably comprise Velcro straps attached to each side of the back support member in such a manner that they are adapted to extend around each of the ladder hand rails in such a manner as to maintain detachable securement therewith. A lower strap is also affixed to the back support member at a position below the main support bar. The lower strap device is designed to surround and engage a ladder step therebelow in order to further affix the water therapy back traction apparatus with respect to the swimming pool ladder in a detachable manner. A lower spacer member is also secured to the back support member at a position below the main support bar in such a manner as to be adapted to be positioned in abutment with respect to the ladder in order to maintain the back support member oriented in a generally vertically extending direction to facilitate support and use thereof.

A first arm member is detachably secured to the back support member and extends outwardly at a position approximately horizontally therefrom opposite from the ladder attachment device in order to be positionable beneath the arm of a user to facilitate supporting of the user. This first arm is preferably adapted to be detachably secured extending into the first slot in order to allow for horizontal adjustment of the positioning thereof. This apparatus provides the first arm adjustment capability.

In a similar manner a second arm device is detachably secured to the back support member and extends outwardly approximately horizontally therefrom oppositely from the ladder attachment device. In this manner it is preferably positionable beneath the arm of a user in order to facilitate supporting of the user in the user receiving zone defined between the two arms and adjacent the back support member. The horizontally extending slot allows the second arm means to be laterally adjustable.

It is an object of the present invention to provide a water therapy back traction apparatus wherein permanent securement to the decking of a swimming pool is a first design.

It is an object of the present invention to provide a water therapy back traction apparatus wherein detachable securement with respect to a conventional swimming pool ladder is an alternative embodiment.

It is an object of the present invention to provide a water therapy back traction apparatus wherein a user's body is suspended in a slightly elevated position within a water swimming pool to control downwardly directed traction forces.

It is an object of the present invention to provide a water therapy back traction apparatus wherein a user's body is supported in the underarm area above a first arm member and a second arm member to provide downwardly directed traction forces.

It is an object of the present invention to provide a water therapy back traction apparatus wherein the buoyancy of water is utilized to limit the amount of gravitational pull on a user's body and thereby provide a means for very careful and accurate control of the magnitude of traction therapy force being used.

It is an object of the present invention to provide a water therapy back traction apparatus wherein the number of moving parts is minimized.

It is an object of the present invention to provide a water therapy back traction apparatus wherein the maintenance requirements are minimized.

It is an object of the present invention to provide a water therapy back traction apparatus wherein the cost of ongoing maintenance is minimal.

It is an object of the present invention to provide a water therapy back traction apparatus wherein a user can perform numerous exercises within the water for aiding in the overall health of a user such as for facilitating circulation within the hands and feet as well as relieving back pain and leg pain.

BRIEF DESCRIPTION OF THE DRAWINGS

While the invention is particularly pointed out and distinctly claimed in the concluding portions herein, a preferred embodiment is set forth in the following detailed description which may be best understood when read in connection with the accompanying drawings, in which:

DETAILED DESCRIPTION OF THE PREFERRED EMBODIMENT

Figure 1:
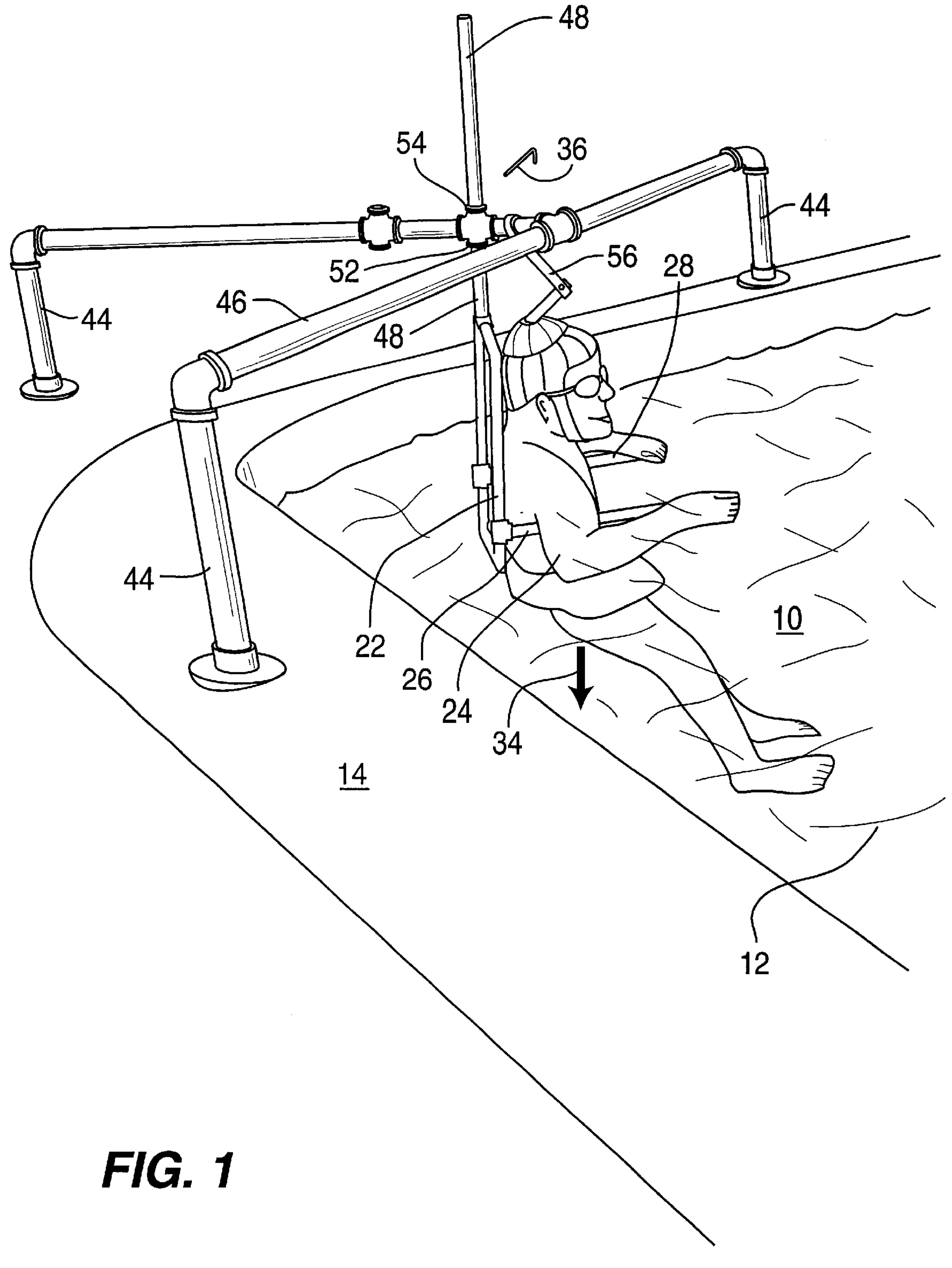
FIG. 1 is a perspective illustration of an embodiment of the water therapy back traction apparatus of the present invention shown installed permanently upon the decking of a swimming pool.

The present invention provides a therapy device for a person's back which utilizes the water 12 within a swimming pool 10 for increasing the effectiveness of the therapy and providing many exercise options and varieties of types of therapy available.

The apparatus of the present invention is designed to be usable with a conventional swimming pool 10 with a decking 14 extending generally horizontally and peripherally around the water 12 of pool 10. It also provides an apparatus which is portable and is detachably secured with respect to a ladder for facilitating the back therapy apparatus. Such a conventional ladder 16 will include hand rails 18 and steps 20 both of which are secured to maintain stability of the traction apparatus.

The basic construction of the traction apparatus includes a back support member 22 which is designed to be placed in abutment with the back of a user 24. A first arm 26 and a second arm 28 are secured with respect to the back support member 22 and extend approximately horizontally therefrom. The user 24 should place the first arm 26 and second arm 28 below his armpits to facilitate support of his body during the time of application of traction.

The user will be positioned within a user receiving zone 30 during the therapy session. This user receiving zone 30 is defined at a position between the first arm 26 and the second arm 28 and adjacent to the back support member 22. When a person is positioned within the user receiving zone 30 the first arm and second arm 26 and 28 will be immediately below the armpit area of a user and the user's back will be in abutment with respect to the back support member 22.

The present invention provides a suspension apparatus 32 for the purpose of suspending the user receiving zone 30 and the back support member 22 thereadjacent at a slightly elevated position within the water 12 of a swimming pool 10. The suspension apparatus makes use of the body weight of the user to apply traction to the back of the user 24 and at the same time makes use of the buoyancy of the water 12 to support most of the user's weight. In this manner the controlled amount of traction therapy force can be exerted along the arrows 34.

Positioning of the suspension apparatus 32 with respect to the water level 12 is a critical aspect of the present invention. For this purpose a suspension adjustment means 36 is included in all embodiments of the present invention for carefully and accurately controlling the relative position of the user receiving zone 30 as compared to the level of the water 12.

A first arm adjustment means 38 is also included for the purposes of varying the relative position of the first arm 26 relative to the back support member 22. At the same time a second arm adjustment means 40 is preferably included for varying the relative position of the second arm 28 with respect to the back support member 22. By providing this lateral movability in both the first arm 26 and the second arm 28 the lateral dimension of the user receiving zone 30 can be varied such as to make the apparatus usable with individuals of various different sizes including both men and women, children, adults, young people and older people.

Figure 2:
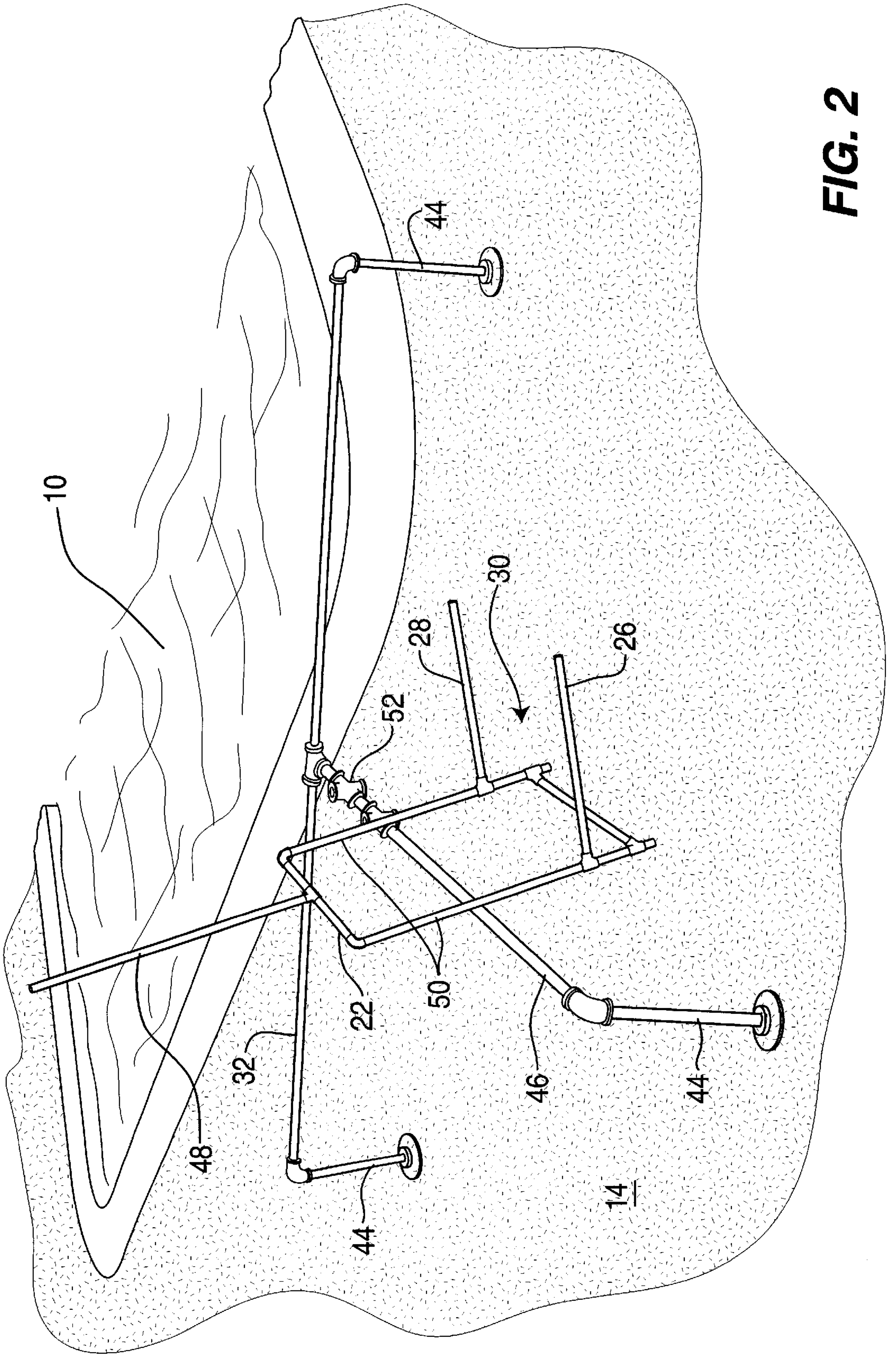
FIG. 2 is an illustration of the apparatus of FIG. 1 shown prior to deployment thereof.
Figure 3:
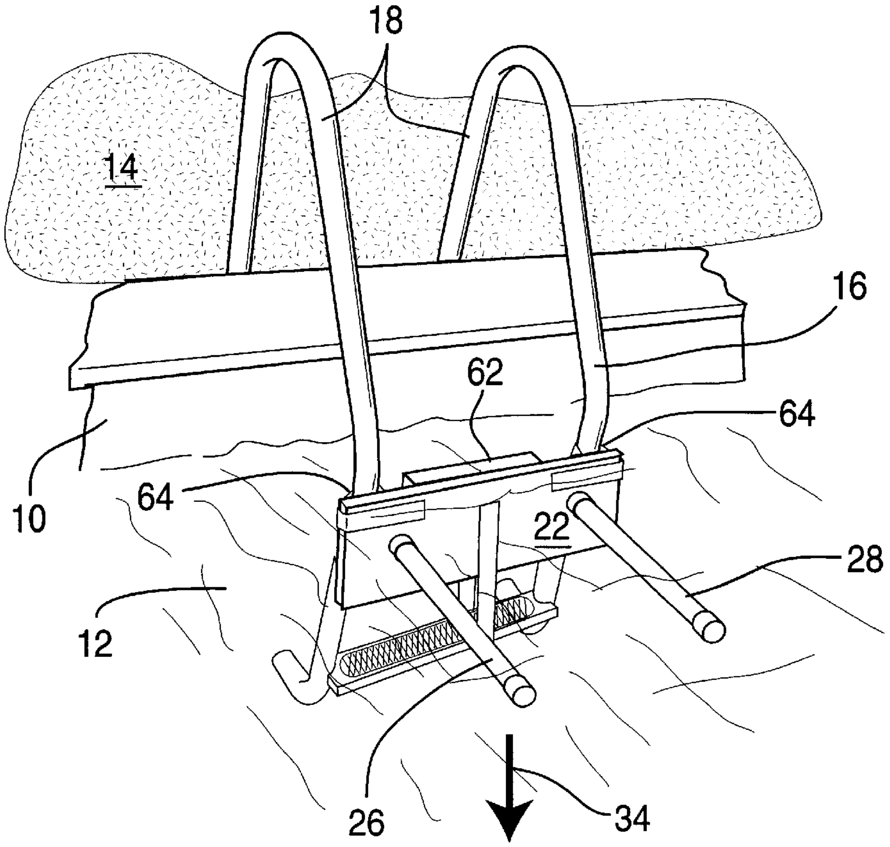
FIG. 3 is a front perspective of an alternative embodiment of the present invention showing the water therapy back traction apparatus secured in place with respect to a conventional swimming pool ladder.
Figure 4:
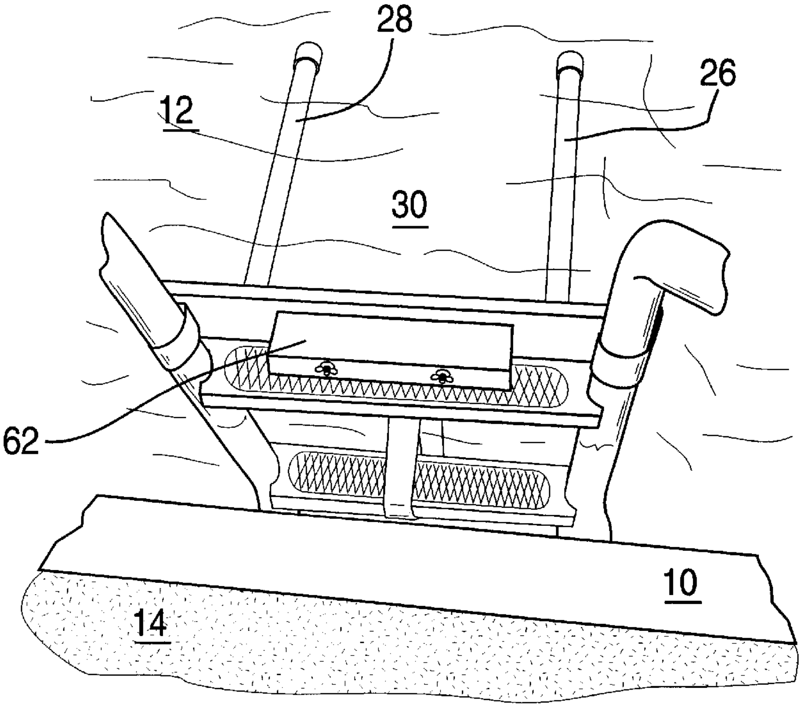
FIG. 4 is a top plan view of the embodiment shown in FIG. 3.
Figure 5:
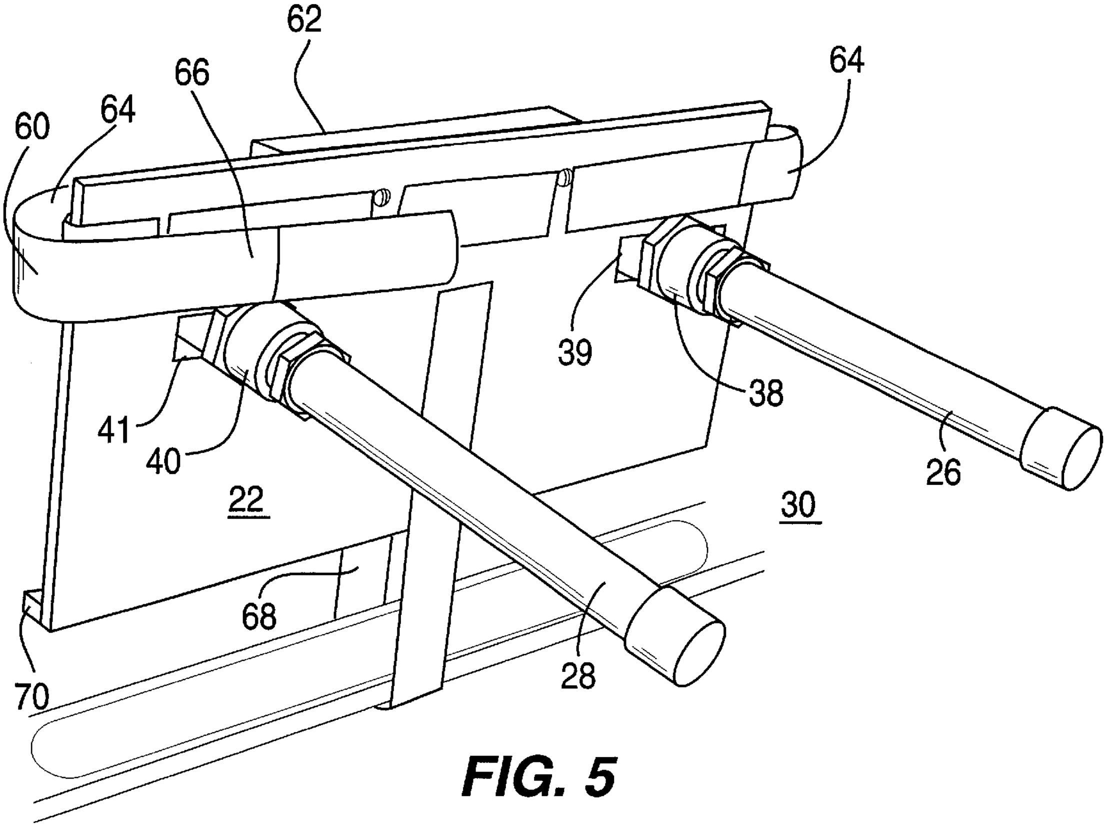
FIG. 5 is a front perspective illustration of the embodiment of the water therapy back traction apparatus shown in FIG. 3.
Figure 6:
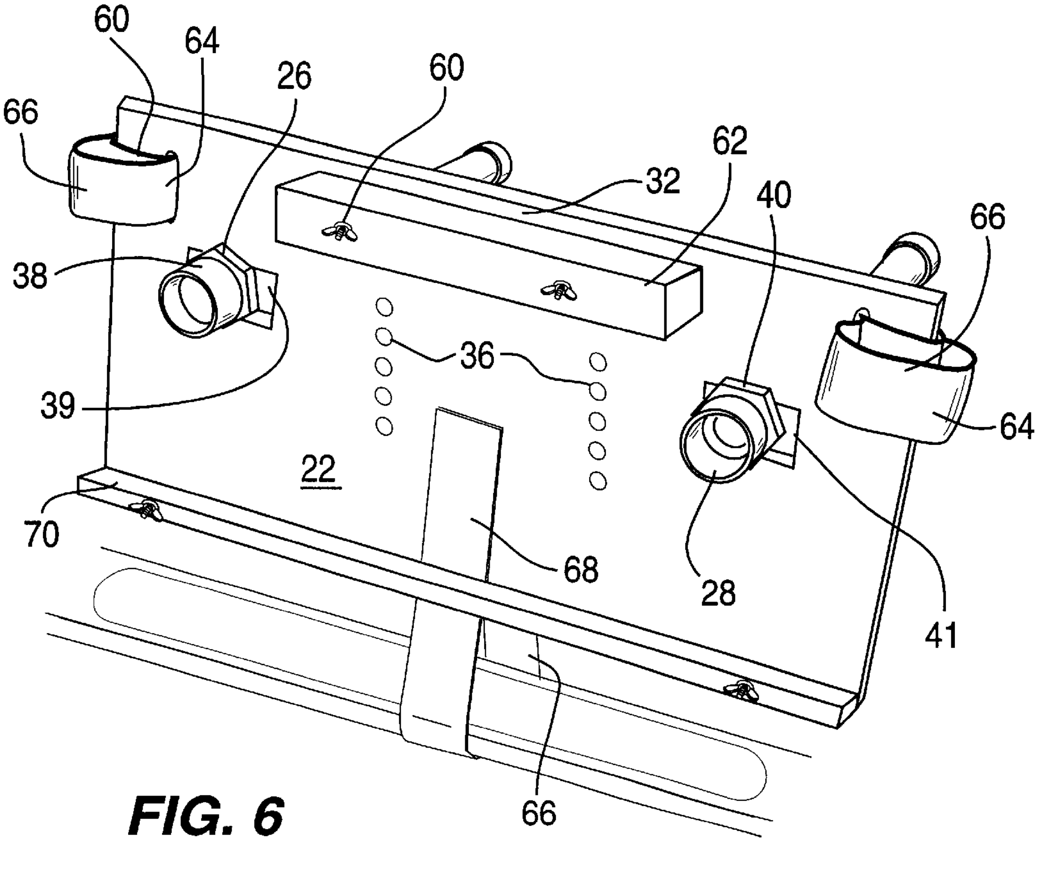
FIG. 6 is a rear plan view of the embodiment shown in FIG. 3.

The present invention discloses a permanent as well as a portable configuration for the water therapy apparatus disclosed herein. The permanent apparatus is shown in FIGS. 1 and 2 and includes a plurality of mounting leg members 44 detachably secured with respect to the decking 14 of the swimming pool 10. A boom 46 is secured to these mounting leg members 44 and extends over the water area. A mounting shaft 48 is adjustably secured with respect to the boom 46 in such a manner that the shaft extends downwardly. The mounting shaft 48 is also attached with respect to the back support member 22 for the positioning of the back support member 22 as well as the user receiving zone 30 extending partially into the water therebelow.

In the preferred configuration as shown in FIGS. 1 and 2 the back support member 22 will comprise an open frame member to facilitate the flow of water around the body of a user during a therapy session. Relative vertical positioning of the back support member 22 with respect to the water level 12 is important and for this purpose a mounting aperture 52 is preferably defined within the boom 46. Mounting aperture 52 is designed to receive the mounting shaft 48 extending thereinto. A set screw or retaining bolt 54 may extend into the mounting aperture or adjacent to the mounting aperture for the purpose of retaining the mounting shaft 48 at one or more of various adjustable vertical positions. In this manner the relative positioning of the back support member 22 with respect to the water level 12 in the permanent configurations of the water therapy back traction apparatus of the present invention as shown in FIGS. 1 and 2 can be carefully controlled. A head traction member 56 can also be included in the permanent or detachable unit for the purposes of relieving downward pressure from the head of a user and treating higher areas of the backbone.

In the portable embodiment as shown in FIGS. 3 through 6 a ladder attachment apparatus 60 is included for detachably securing the back support member 22 with respect to a ladder 16 and in particular with respect to the vertically extending hand rails 18 and the steps 20 defined thereon. In this particular configuration a main support bar 62 is secured to the back support member 22 and is adapted to rest upon the upper surface of a step 20 of a ladder 16 for supporting of the back support member 22 thereon. A rail securement apparatus 64 is also included preferably in the form of a plurality of Velcro straps 66 each of which is securable with respect to the back support member 22 as well as being detachably securable with respect to the vertically extending hand rails 18. A lower strap means 68 may also be included for securing the back support member 22 with respect to a lower step 20 of ladder 16 at a position below the main support bar 62. This lower strap means 68 is detachable with respect to this step 20 which is positioned below the step upon which the may support bar 62 rests. A lower spacer member 70 is also preferably included for spacing the lower portion of the back support member 22 slightly outwardly from the ladder 16 and in particular from the steps 20 and the hand rails 18 thereof in order to facilitate ease in positioning of the body of a user 24 within the user receiving zone 30 when the portable water therapy back traction apparatus of the present invention is secured to a ladder 16 of a conventional swimming pool 10.

The above description shows the use of the water therapy device specifically placed within a swimming pool. However, it should be appreciated that this device can be usable with any body of water having the necessary ladder and/or side wall elements that may be required for a specific application of the device. Although particularly useful within a swimming pool, use of this device within any type of water containment chamber is hereby anticipated as a part of this invention.

While particular embodiments of this invention have been shown in the drawings and described above, it will be apparent, that many changes may be made in the form, arrangement and positioning of the various elements of the combination. In consideration thereof it should be understood that preferred embodiments of this invention disclosed herein are intended to be illustrative only and not intended to limit the scope of the invention.

I claim:

1. A water therapy back traction apparatus for use with a conventional water swimming pool having surrounding decking and a ladder extending downwardly therein with vertical ladder hand rails and steps extending therebetween comprising:

A. a back support member extending generally vertically for receiving the back of a user in abutment therewith for facilitating supporting thereof;

B. a first arm means secured to said back support member and extending outwardly approximately horizontally therefrom to be positionable beneath the arm of a user to facilitate supporting the user;

C. a second arm means secured to said back support member and extending outwardly approximately horizontally therefrom to be positionable beneath the arm of a user to facilitate supporting of the user, said second arm means being located at a position spatially disposed from said first arm means to define a user receiving zone therebetween and with said back support member; and D. a suspension apparatus adapted to be secured with respect to a swimming pool and attached to said back support member for suspending both the back support member and a user in abutment therewith positioned within said user receiving zone at least partially within the water of the swimming pool at an elevated position to impart traction therapy forces on the back of a user; and E. a ladder attachment means for selectively affixing said back support member securely with respect to a ladder positioned adjacent to and extending into the swimming pool water.

2. A water therapy back traction apparatus for use with a conventional water swimming pool having surrounding decking and a ladder extending downwardly therein with vertical ladder hand rails and steps extending therebetween as defined in claim 1 wherein said ladder attachment means comprises:

A. a main support bar detachably securable to said back support member and extending outwardly therefrom opposite from said first arm means and said second arm means, said main support bar being adapted to be positioned upon a ladder step for supporting said back support member with respect thereto;

B. a rail securement means attached to said back support member and extending outwardly therefrom adjacent said main support bar in order to engage the vertical ladder hand rails and further affix said back support member with respect to the ladder.

3. A water therapy back traction apparatus for use with a conventional water swimming pool having surrounding decking and a ladder extending downwardly therein with vertical ladder hand rails and steps extending therebetween as defined in claim 2 wherein said rail securement means comprises a Velcro strap means attached to said back support member and adapted to extend around each of the ladder hand rails for maintaining detachable securement therebetween.

4. A water therapy back traction apparatus for use with a conventional water swimming pool having surrounding decking and a ladder extending downwardly therein with vertical ladder hand rails and steps extending therebetween as defined in claim 2 wherein said main support bar is detachably secured to said back support member to facilitate adjustment in the relative secured positioning therebetween in order to provide the capability to control the affixed position of the back support member with respect to the level of the water within the swimming pool to control the downwardly directed traction therapy forces.

5. A water therapy back traction apparatus for use with a conventional water swimming pool having surrounding decking and a ladder extending downwardly therein with vertical ladder hand rails and steps extending therebetween as defined in claim 4 wherein said main support bar is adjustably with respect to said back support member in a generally vertically extending direction to facilitate adjustment in the vertical positioning of said user receiving zone with respect to the swimming pool ladder and the level of water in the swimming pool to facilitate control of the back traction forces exerted on a user.

6. A water therapy back traction apparatus for use with a conventional water swimming pool having surrounding decking and a ladder extending downwardly therein with vertical ladder hand rails and steps extending therebetween as defined in claim 1 further comprising a lower strap means affixed to said back support member below said main support bar and adapted to surround and engage a ladder step therebelow to further affix the water therapy back traction apparatus with respect to a swimming pool ladder detachably.

7. A water therapy back traction apparatus for use with a conventional water swimming pool having surrounding decking and a ladder extending downwardly therein with vertical ladder hand rails and steps extending therebetween as defined in claim 1 further comprising a head traction member adapted to be secured with respect to a swimming pool and extending downwardly toward said user receiving zone, said head traction member adapted to be secured to the head of a user positioned within said user receiving zone to apply traction to the head of a user by resisting downward movement thereof.

8. A water therapy back traction apparatus for use with a conventional water swimming pool having surrounding decking and a ladder extending downwardly therein with vertical ladder hand rails and steps extending therebetween as defined in claim 1 further including a lower spacer member secured to said back support member at a position below said main support bar and adapted to be positioning in abutment with respect to a ladder step to maintain said back support member orientated in a generally vertically extending direction to facilitate use thereof.

9. A water therapy back traction apparatus for use with a conventional water swimming pool having surrounding decking and a ladder extending downwardly therein with vertical ladder hand rails and steps extending therebetween as defined in claim 1 wherein said back support member further defines a first arm slot means and a second arm slot means extending generally horizontally therein and spatially disposed horizontally with respect to one another, said first arm means adapted to be detachably securable into said first arm slot means to allow horizontal adjustment in the positioning thereof with respect to said back support member, said second arm means adapted to be detachably securable into said second arm slot means to allow horizontal adjustment in the positioning thereof with respect to said back support member, adjustment in the horizontal positioning of said first arm means relative to said second arm means facilitating adjustment in the horizontal size of said user receiving zone to accommodate different sized users.

10. A water therapy back traction apparatus for use with a conventional water swimming pool having surrounding decking and a ladder extending downwardly therein with vertical ladder hand rails and steps extending therebetween comprising:

A. a back support member extending generally vertically for receiving the back of a user in abutment therewith for facilitating supporting thereof, said back support member further defining a first arm slot means and a second arm slot means extending generally horizontally therein and spatially disposed horizontally with respect to one another;

B. a ladder attachment means attached to said back support member for selectively affixing thereof securely with respect to a ladder positioned adjacent to and extending into the swimming pool water, said ladder attachment means including;

(1) a main support bar detachably securable to said back support member and extending outwardly therefrom, said main support bar being detachably securable with respect to said back support member at a plurality of positions relative thereto in order to facilitate vertical adjustment in the relative secured positioning between said main support bar and said back support member in order to provide the capability to control the affixed position of the back support member with respect to the height of the water within the swimming pool to provide control of the downwardly directed traction therapy forces, said main support bar being adapted to be positioned in abutment upon a ladder step for supporting said back support member with respect thereto;

(2) a rail securement means attached to said back support member and extending outwardly therefrom adjacent said main support bar in order to engage the vertical ladder hand rails and further affix said back support member detachably with respect to the ladder, said rail securement means including a Velcro strap means attached to said back support member and adapted to extend around each of the ladder hand rails for maintaining detachable securement therebetween;

(3) a lower strap means affixed to said back support member below said main support bar and adapted detachably to surround and engage a ladder step therebelow to further affix the water therapy back traction apparatus with respect to a swimming pool ladder selectively;

(4) a lower spacer member secured to said back support member at a position below said main support bar and adapted to be positioning in abutment with respect to a ladder step to maintain said back support member orientated in a generally vertically extending direction to facilitate use thereof;

B. a first arm means detachably secured to said back support member and extending outwardly approximately horizontally therefrom oppositely from said ladder attachment means in order to be positionable beneath the arm of a user to facilitate supporting the user, said first arm means adapted to be detachably securable extending into said first arm slot means to allow horizontal adjustment in the positioning thereof with respect to said back support member;

C. a first arm adjustment means for providing adjustability of positioning of said first arm means with respect to said back support member in order accommodate different size users;

D. a second arm means detachably secured to said back support member and extending outwardly approximately horizontally therefrom oppositely from said ladder attachment means in order to be positionable beneath the arm of a user to facilitate supporting of the user, said second arm means being located at a position spatially disposed from said first arm means to define a user receiving zone therebetween and with said back support member, said second arm means adapted to be detachably securable extending into said second arm slot means to allow horizontal adjustment in the positioning thereof with respect to said back support member;

E. a second arm adjustment means for providing adjustability of positioning of said second arm means with respect to said back support member in order accommodate different size users by varying the lateral size of said user receiving zone;

F. a suspension apparatus adapted to be secured to a swimming pool and attached to said back support member for suspending both the back support member and a user in abutment therewith positioned within said user receiving zone at least partially within the water of the swimming pool at an elevated position to impart traction therapy forces on the back of a user; and G. a suspension adjustment means operatively attached to said suspension apparatus and said back support member to provide adjustable positioning therebetween in order to control the positioning of a user located within said user receiving zone relative to the swimming pool water.

* * * * *